United States Patent [19]
Ochi

[11] Patent Number: 5,797,347
[45] Date of Patent: Aug. 25, 1998

[54] ABSORBENT PANEL FOR PET ANIMALS

[75] Inventor: Kengo Ochi, Ehime-ken, Japan

[73] Assignee: Uni-Charm Corporation, Ehime-ken, Japan

[21] Appl. No.: 691,048

[22] Filed: Aug. 1, 1996

[30] Foreign Application Priority Data

Aug. 2, 1995 [JP] Japan .................. 7-197730

[51] Int. Cl.⁶ .................. A01K 1/035; A61F 13/15
[52] U.S. Cl. .................. 119/169; 605/385.1
[58] Field of Search .................. 119/169, 171, 119/172, 526; 605/367, 370, 385.1

[56] References Cited

U.S. PATENT DOCUMENTS

| | | | |
|---|---|---|---|
| 2,720,861 | 10/1955 | Stroup et al. | 119/526 |
| 3,284,273 | 11/1966 | Prentice | 119/169 X |
| 4,041,950 | 8/1977 | Jones, Sr. | 604/385.1 X |
| 4,994,052 | 2/1991 | Kimura | 604/385.1 X |
| 5,141,794 | 8/1992 | Arroyo | 604/385.1 X |
| 5,207,662 | 5/1993 | James | 604/385.1 X |
| 5,429,628 | 7/1995 | Latimer et al. | 604/385.1 X |
| 5,449,352 | 9/1995 | Nishino et al. | 604/370 X |
| 5,582,603 | 12/1996 | Difilippantonio et al. | 604/385.1 X |

FOREIGN PATENT DOCUMENTS 4-673  1/1992  Japan .

Primary Examiner—Jack W. Lavinder
Assistant Examiner—Yvonne R. Abbott
Attorney, Agent, or Firm—Lowe Hauptman Gopstein Gilman & Berner

[57] ABSTRACT

An absorbent panel for pet animals such as dogs and cats comprising a liquid-permeable topsheet, a liquid-impermeable backsheet and a liquid-absorbent core panel therebetween, the core panel comprises a relatively thin central region and a relatively thick side region.

12 Claims, 2 Drawing Sheets

ABSORBENT PANEL FOR PET ANIMALS

BACKGROUND OF THE INVENTION

The present invention relates to an absorbent panel for pet animals such as dogs and cats and, more particularly, to a panel used to absorb and hold liquid excretion, for example, urine of such pet animals boarded.

Japanese Laid-Open Utility Model Application No. Hei4-673 discloses an absorbent panel for pet animals comprising a liquid-absorbent sheet having two sheets of blotting paper and superabsorptive polymer powders disposed there between above and a water-proof sheet bonded to a lower surface of the liquid-absorbent sheet.

However, most of the conventional urine absorbent sheets such as the sheet disclosed in the above-mentioned absorb urine discharged onto a central region of the sheet and have no effective means to avoid sideway leakage of urine possibly discharged onto a peripheral region of the sheet. Pet animals insufficiently trained to use such sheets often urinate on the peripheral region of the sheet and consequently contaminate the room in which the panel is placed. Thus the aimed effect of the absorbent panel is not always achieved.

Accordingly, it is a principal object of the invention to avoid sideward leakage of urine from the peripheral region of the absorbent panel.

SUMMARY OF THE INVENTION

According to the invention, there is provided an absorbent panel for pet animals comprising a liquid-permeable topsheet, a liquid-impermeable backsheet and a liquid-absorbent core panel disposed between the two sheets, wherein the core panel comprises a relatively thin central region and a relatively thick side edge region which occupies more than half of a periphery of the core panel and has a width at least 20 mm.

According to a preferred embodiment of the invention, the side edge region is at least 1.5 times as thick as the central region and contains superabsorptive polymer powders at least of 30 g/m$^3$.

DETAILED DESCRIPTION OF THE PREFERRED EMBODIMENTS

Figure 1:
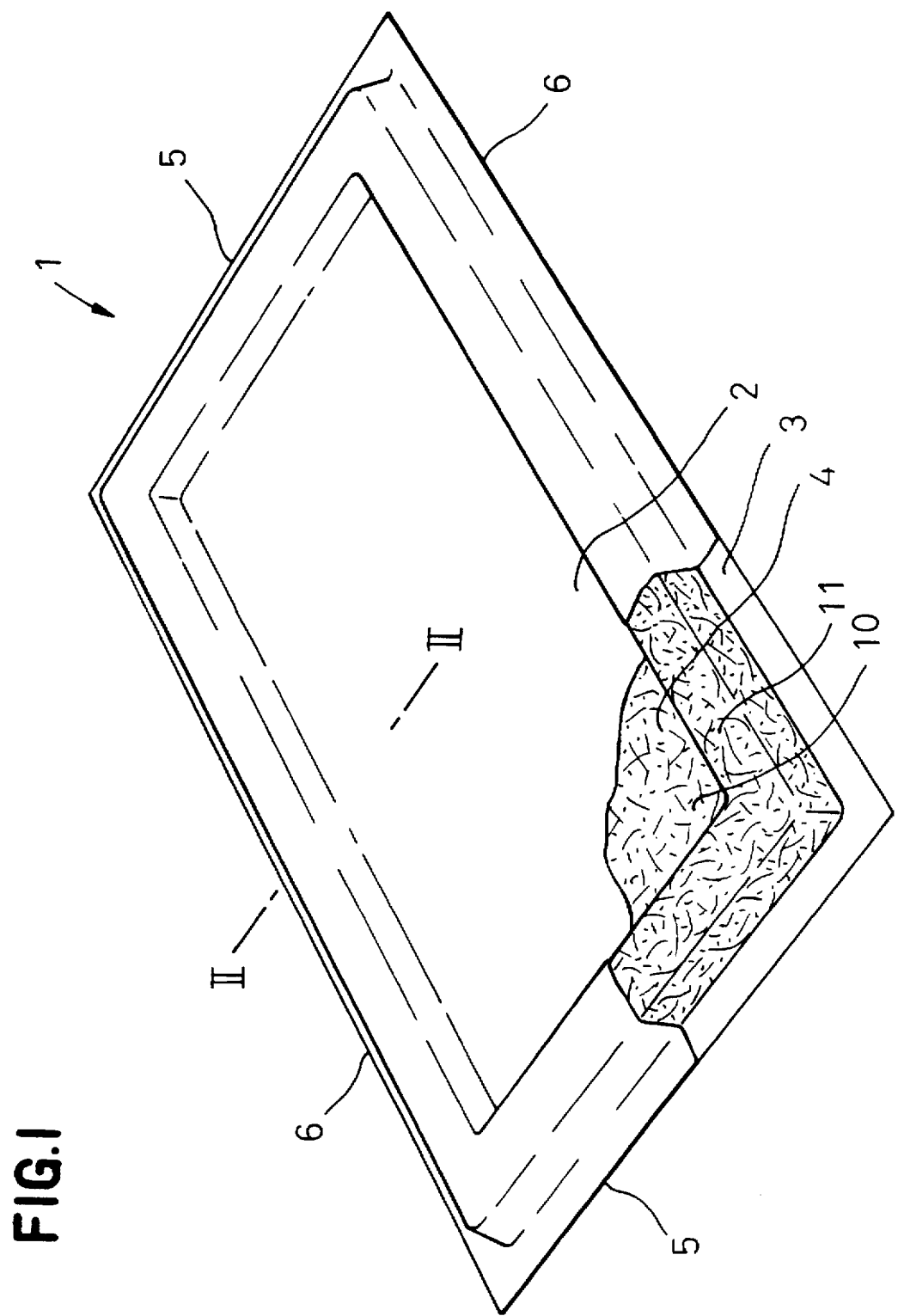
FIG. 1 is a perspective view showing an absorbent panel of the invention as partially broken away.

Referring to FIG. 1, a rectangular absorbent panel 1 is principally used for dogs or cats bred indoors and comprises a liquid-permeable topsheet 2 made of a nonwoven fabric, a liquid-impermeable backsheet 3 made of a plastic film and a liquid-absorbent core panel 4 disposed between the two sheets 2, 3. The panel 1 is defined by longitudinally opposite ends 5 and transversely opposite side edges 6. The panel 1 has a relatively thin central region 10 and relatively thick side edge region 11 completely surrounding the central region 10. The top- and backsheets 2, 3 extend outward beyond a peripheral edge of the core panel 4 and have their opposing inner surfaces watertightly heat-sealed to each other.

Figure 2:
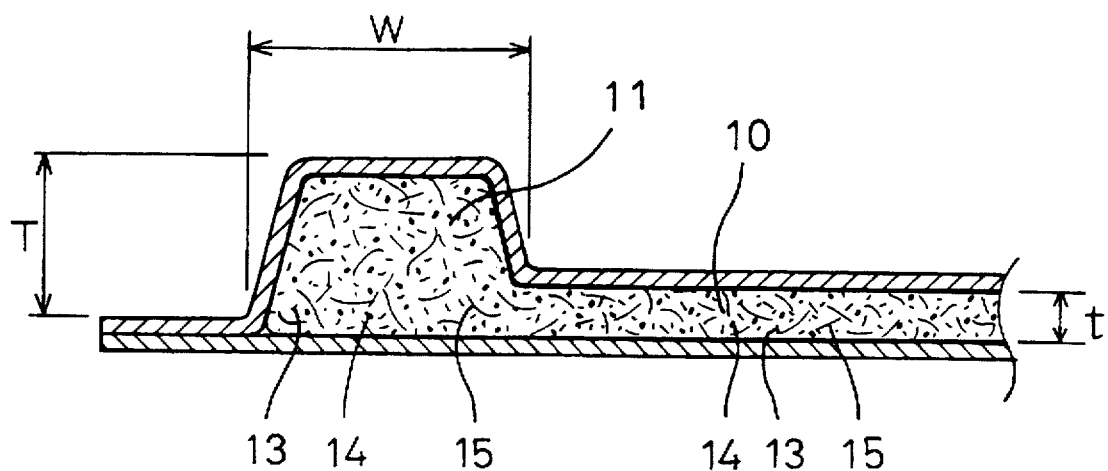
FIG. 2 is a sectional view taken along a line II—II in FIG. 1.

Referring to FIG. 2, the central region 10 of the core panel 4 has a thickness 't' while the side edge region 11 surrounding the central region 10 presents a trapezoidal cross-section having a width 'W' of at least of 20 mm and a thickness 'T' at least equal to 't'×1.5. While the thickness 't' may be appropriately selected, it is preferred to select the thickness 't' in a range of 1 to 10 mm, and the thickness 'T' is preferably selected in a range of 1.5 to 20 mm. The central region 10 mainly comprises fluff pulp fibers 13 and may comprise additional materials such as superabsorptive polymer powders 14 up to 15 g/m$^3$ and thermoplastic synthetic fibers 15 up to 20% by weight. In the core panel 4, the superabsorptive polymer powders 14 are preferably distributed with an unevenly high density adjacent the backsheet 3 and, particularly in the side edge region 11, 50 or higher % by weight of the polymer powders 14 is preferably concentrated into a lower half of its thickness. It is assured thereby that a quantity of urine having been quickly absorbed by the fluff pulp fibers 13 moves into the superabsorptive polymer powders 14 without sideward leakage from the absorbent panel 1. The top- and backsheets 2, 3 are respectively bonded at desired locations to the core panel 4 or bonded to each other on a predetermined line along which the core panel 4 has been partially cut away so as to maintain the core panel 4 in a desired configuration. An embodiment of the core panel 4 including thermoplastic synthetic fibers advantageously promotes spreading of urine among the pulp fibers 13, allows the top- and backsheets 2, 3 to be bonded to the core panel 4 by means of heat-sealing and allows the core panel 4 to be molded under the effect of heating.

Figure 3:
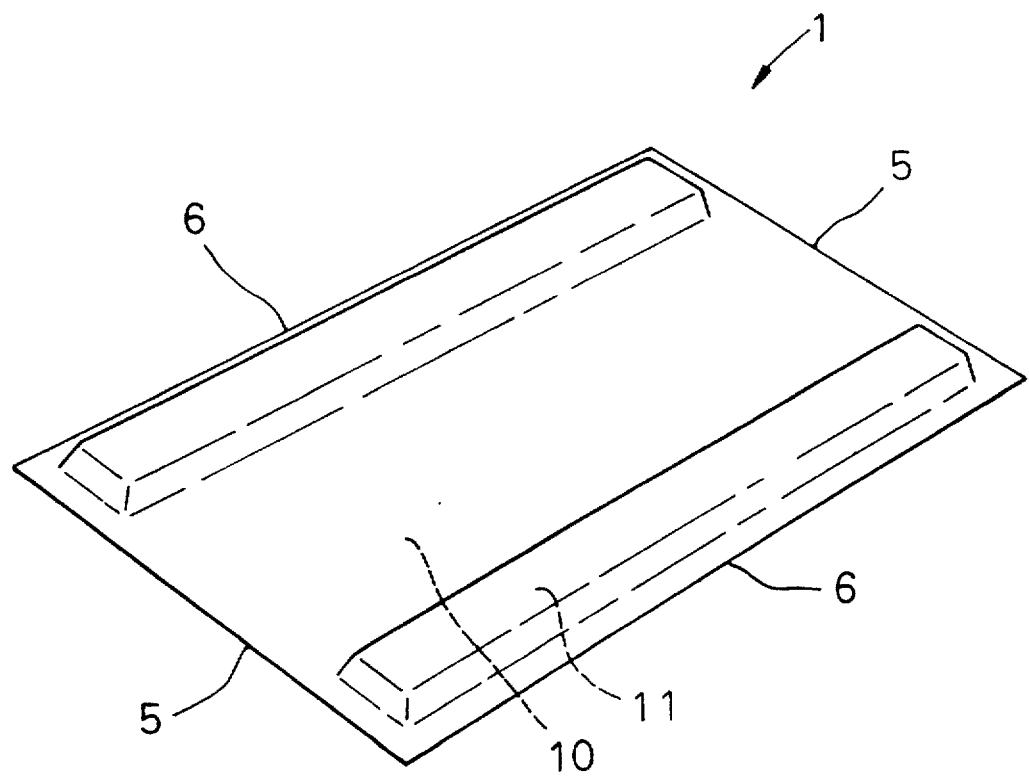
FIG. 3 is a perspective view of an alternative embodiment of the absorbent panel.

Referring to FIG. 3, in this rectangular panel 1, the side edge region 11 has said thickness 'T' merely along transversely opposite side edges 6 and longitudinally opposite ends 5 substantially the same thickness as that of the central region 10.

To implement the invention, not only a nonwoven fabric but also a perforated plastic film or the like may be used as material for topsheet 2. Bonding of the respective members can be achieved by using an adhesive agent such as hot melt type adhesive or heat-sealing technique so far as the heat-sealable material is concerned.

The absorbent panel of the invention has a unique arrangement in that the panel 1 is thicker in the side edge region 11 than in the central region 10 and a substantially larger quantity of the superabsorptive polymer powders is distribute d in the side edge region 11. Such an arrangement effectively blocks a quantity of liquid excretion which otherwise might tend to leak sideways from the panel periphery, by allowing then causes the superabsorptive polymer powders to absorb such liquid excretion and thereby to prevent it from further moving sideways. The absorbent panel of the invention can be used for pet animals insufficiently trained to use this panel without contaminating the room in which this panel is placed, since an undesirable sideward leakage of liquid excretion is reliably avoided even if liquid excretion is discharged onto the panel at a location adjacent the side edge region thereof.

What is claimed is:

1. An absorbent panel for pet animals, comprising a liquid-permeable topsheet, a liquid-impermeable backsheet and a liquid-absorbent core panel disposed between said topsheet and backsheet, wherein said core panel comprises a relatively thin central region and a relatively thicker side edge region , an upper surface of said absorbent panel exposed to ambient environment being defined by said topsheet which is profiled such that a periphery thereof overlying said thicker side edge region is raised relative to a center portion of said topsheet overlying said central region, said center portion thereby being depressed, wherein said side edge region contains superabsorptive polymer powders at least of 30 g/m³, wherein said polymer powders are distributed with an unevenly high density adjacent said backsheet.

2. The absorbent panel of claim 1, wherein said relatively thicker side region occupies more than half of a periphery of said core panel, said thicker side region having a width of at least 20 mm.

3. The absorbent panel of claim 1, wherein said topsheet is in direct contact with said core panel thin central region.

4. The absorbent panel of claim 1, wherein said thicker side region extends along all sides of said core panel.

5. The absorbent panel of claim 1, wherein said thicker side region extends along two parallel sides of said core panel.

6. The absorbent panel of claim 1, wherein said absorbent panel is a rectangular panel.

7. An absorbent panel for pet animals, comprising a liquid-permeable topsheet, a liquid-impermeable backsheet and a liquid-absorbent core panel disposed between said topsheet and backsheet, wherein said core panel comprises a relatively thin central region and a relatively thicker side edge region, an upper surface of said absorbent panel exposed to ambient environment being defined by said topsheet which is profiled such that a periphery thereof overlying said thicker side edge region is raised relative to a center portion of said topsheet overlying said central region, said center portion thereby being depressed, wherein said side region includes polymer powders concentrated in a lower half of a thickness of side region.

8. The absorbent panel of claim 7, wherein said relatively thicker side region occupies more than half of a periphery of said core panel, said thicker side region having a width of at least 20 mm.

9. The absorbent panel of claim 7, wherein said topsheet is in direct contact with said core panel thin central region.

10. The absorbent panel of claim 7, wherein said thicker side region extends along all sides of said core panel.

11. The absorbent panel of claim 7, wherein said thicker side region extends along two parallel sides of said core panel.

12. The absorbent panel of claim 7, wherein said absorbent panel is a rectangular panel.

* * * * *